United States Patent
Yoshida

(10) Patent No.: US 8,740,779 B2
(45) Date of Patent: Jun. 3, 2014

(54) IMAGING DEVICE AND METHOD OF CLEANING AN ILLUMINATION WINDOW OF THE IMAGING DEVICE

(75) Inventor: Koji Yoshida, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 132 days.

(21) Appl. No.: 13/198,583

(22) Filed: Aug. 4, 2011

(65) Prior Publication Data

US 2012/0059222 A1     Mar. 8, 2012

(30) Foreign Application Priority Data

Sep. 6, 2010    (JP) .................. 2010-198512

(51) Int. Cl.
*A61B 1/06*     (2006.01)
*A61B 1/12*     (2006.01)

(52) U.S. Cl.
USPC .......................................... 600/177; 600/157

(58) Field of Classification Search
USPC .......... 600/108, 129, 156–160, 176, 177, 178
See application file for complete search history.

(56) References Cited

U.S. PATENT DOCUMENTS

| | | | |
|---|---|---|---|
| 4,838,246 A * | 6/1989 | Hahn et al. ............ | 600/108 |
| 5,630,795 A * | 5/1997 | Kuramoto et al. ............ | 604/30 |
| 5,637,075 A | 6/1997 | Kikawada | |
| 5,782,751 A * | 7/1998 | Matsuno ............ | 600/157 |
| 6,309,347 B1 * | 10/2001 | Takahashi et al. ............ | 600/159 |
| 2006/0161047 A1 * | 7/2006 | Miyoshi ............ | 600/157 |
| 2007/0249907 A1 * | 10/2007 | Boulais et al. ............ | 600/179 |

FOREIGN PATENT DOCUMENTS

| | | |
|---|---|---|
| JP | 7-289514 A | 11/1995 |
| JP | 9-253034 A | 9/1997 |
| JP | 10-225426 (A) | 8/1998 |
| JP | 11-221190 (A) | 8/1999 |
| JP | 2002-272683 (A) | 9/2002 |
| JP | 2008-148935 (A) | 7/2008 |
| JP | 2008-279202 A | 11/2008 |
| JP | 2009-279291 A | 12/2009 |

OTHER PUBLICATIONS

Notice of Grounds for Rejection dated Dec. 10, 2013, with English translation.
Notice of Grounds for Rejection dated Feb. 25, 2014, with English translation.

* cited by examiner

*Primary Examiner* — Philip R Smith
(74) *Attorney, Agent, or Firm* — McGinn IP Law Group, PLLC

(57) ABSTRACT

In an imaging device for capturing an image by applying illuminating light emitted from a light source to a part to be observed through a light exit window and receiving light coming from the part to be observed when the illuminating light is applied, a light exit window cleaning unit discharges a liquid toward the light exit window to clean the light exit window in response to an instruction to start application of the illuminating light.

11 Claims, 9 Drawing Sheets

IMAGING DEVICE AND METHOD OF CLEANING AN ILLUMINATION WINDOW OF THE IMAGING DEVICE

BACKGROUND OF THE INVENTION

1. Field of the Invention

The present invention relates to an imaging device for capturing an image with applying illuminating light emitted from a light source to a part to be observed through a light exit window, and a method of cleaning the light exit window of the imaging device.

2. Description of the Related Art

Conventionally, endoscopic systems for observing a tissue in a body cavity are widely known, and electronic endoscopic systems which acquire a normal image by imaging a part to be observed in a body cavity with applying white light and display the normal image on a monitor screen have been put to practical use and are widely used.

As one of such endoscopic systems, an endoscopic system for acquiring a fluorescence image of blood vessels has been proposed, where ICG (indocyanine green) is administered into the body in advance and near-infrared light is applied to a part to be observed to detect fluorescence emitted from the ICG in the blood vessels, in order to check blood vessels that are present at a depth exceeding a certain depth from the surface of a living tissue of the subject and thus do not appear on the normal image.

When an endoscopic surgery is performed with using the above-described type of endoscopic system, smoke or mist adheres to the distal end of the insertion section of the endoscope inserted into the body cavity and may often contaminate the imaging lens and the light exit window of the endoscope. At each such time, the endoscope is pulled out from the body cavity and cleaned.

In particular, the above-described type of endoscopic system, which observes fluorescence in the near-infrared region, usually uses diffused coherent laser light, in order to apply near-infrared laser light to a wide range and to avoid concentration of the near-infrared laser light on the surface of the part to be observed exposed to the near-infrared laser light, and it is generally necessary to provide a light exit window with a large area for the near-infrared light.

Therefore, there is high possibility of the above-described adhesion of contaminants to the light exit window for the near-infrared light, and frequent cleaning of the endoscope is required. However, if the endoscope is pulled out from the body cavity each time contaminants adhere to the light exit window and is again inserted into the body cavity after cleaning, the surgery operation stops during the cleaning and the field of view of the reinserted endoscope is changed from that before, causing significant loss for the time of the surgery operation.

Further, in the case where a light source with a relatively high power density, such as a laser light source, is used in the above-described type of endoscopic system, when contaminants, such as blood, adhere to the light exit window provided at the distal end of the endoscope, the contaminants may be burned by the illuminating light and the burnt contaminants on the light exit window hinder application of necessary illumination. In addition, the burnt contaminants on the light exit window and increase of reflected light from the light exit window may increase the temperature of a light guiding member extending to the light exit window and the light guiding member may be burned.

In order to address such problems, Japanese Unexamined Patent Publication Nos. 2009-279291, 2008-279202, H09-253034 and H07-289514 (hereinafter, Patent Documents 1 to 4), for example, propose endoscopic systems provided with a cleaning mechanism at the distal end of the insertion section of the endoscope, so that the imaging lens and the light exit window can be cleaned without pulling out the insertion section of the endoscope from the body cavity.

With the endoscopic systems disclosed in Patent Documents 1 to 4, when contaminants adhere to the surface of the imaging lens disposed at the distal end of the insertion section during observation of the normal image, for example, the presence of contaminants adhering to the distal end of the insertion section can be checked by the operator by observing the actually captured image. However, when the contaminants adhere only to the light exit window for the near-infrared light during observation of the normal image, for example, the operator does not notice the presence of adhering contaminants. Further, when the observation of the normal image is switched to observation of the fluorescence image, it is also difficult to notice decrease of illuminance since the near-infrared light is invisible, and the above-described problem of burnt contaminants on the light exit window may occur.

SUMMARY OF THE INVENTION

In view of the above-described circumstances, the present invention is directed to providing an imaging device and a method of cleaning a light exit window of the imaging device, which allow cleaning of the light exit window to remove contaminants therefrom at appropriate timing, thereby effectively preventing burning, etc., of contaminants on the light exit window.

An aspect of the method of cleaning a light exit window of an imaging device of the invention is a method of cleaning a light exit window of an imaging device, the imaging device including a light applying unit for applying illuminating light emitted from a light source to a part to be observed through the light exit window, and an imaging unit for capturing an image by receiving light coming from the part to be observed when the illuminating light is applied, the method including: receiving an instruction to start application of the illuminating light; and discharging a liquid toward the light exit window in response to the instruction to start application of the illuminating light.

An aspect of the imaging device of the invention is an imaging device including a light applying unit for applying illuminating light emitted from a light source to a part to be observed through a light exit window, and an imaging unit for capturing an image by receiving light coming from the part to be observed when the illuminating light is applied, the imaging device further including: a light exit window cleaning unit for discharging a liquid toward the light exit window; and a light-application start instruction receiving unit for receiving an instruction to start application of the illuminating light, wherein the light exit window cleaning unit discharges the liquid in response to the instruction to start application of the illuminating light.

In the imaging device of the invention, the light applying unit may include a body cavity insertion section to be inserted into a body cavity, and the light exit window may be provided at a distal end of the body cavity insertion section.

The light applying unit may apply excitation light serving as the illuminating light to the part to be observed through the light exit window, and the imaging unit may capture a fluorescence image by receiving fluorescence emitted from the part to be observed when the excitation light is applied.

The light source may be a laser light source or a LED (Light Emitting Diode) light source.

The imaging unit may receive the light coming from the part to be observed through an imaging lens, and an imaging lens cleaning unit for discharging the liquid toward the imaging lens may be provided separately from the light exit window cleaning unit.

In response to the instruction to start application of the illuminating light, the light exit window cleaning unit may discharge the liquid only from the light exit window cleaning unit among the imaging lens cleaning unit and the light exit window cleaning unit.

The light applying unit may apply excitation light serving as the illuminating light to the part to be observed through the light exit window for the excitation light, and may apply white light serving as the illuminating light to the part to be observed through the light exit window for the white light, the imaging unit may capture a fluorescence image by receiving fluorescence emitted from the part to be observed when the excitation light is applied, and may capture a normal image by receiving reflected light reflected from the part to be observed when the white light is applied, and the light exit window cleaning unit may include a nozzle for discharging the liquid, and the single nozzle may be used to discharge the liquid toward both the light exit window for the excitation light and the light exit window for the white light.

Alternatively, the light applying unit may apply excitation light serving as the illuminating light to the part to be observed through the light exit window for the excitation light, and may apply white light serving as the illuminating light to the part to be observed through the light exit window for the white light, the imaging unit may capture a fluorescence image by receiving, through an imaging lens, fluorescence emitted from the part to be observed when the excitation light is applied, and may capture a normal image by receiving, through the imaging lens, reflected light reflected from the part to be observed when the white light is applied, and the light exit window cleaning unit may include a nozzle for discharging the liquid, and the single nozzle may be used to discharge the liquid toward the light exit window for the excitation light, the light exit window for the white light and the imaging lens.

The light exit window cleaning unit may be disposed at a mantle tube provided around the body cavity insertion section.

According to the method of cleaning a light exit window of an imaging device of the invention, in an imaging device for capturing an image by applying illuminating light emitted from a light source to a part to be observed through a light exit window and receiving light coming from the part to be observed when the illuminating light is applied, a light exit window cleaning unit discharges a liquid toward the light exit window to clean the light exit window in response to an instruction to start application of the illuminating light. In this manner, the light exit window is cleaned every time the illuminating light is applied to the part to be observed, thereby effectively preventing burning of contaminants, etc., on the light exit window.

DESCRIPTION OF THE PREFERRED EMBODIMENTS

Figure 1:
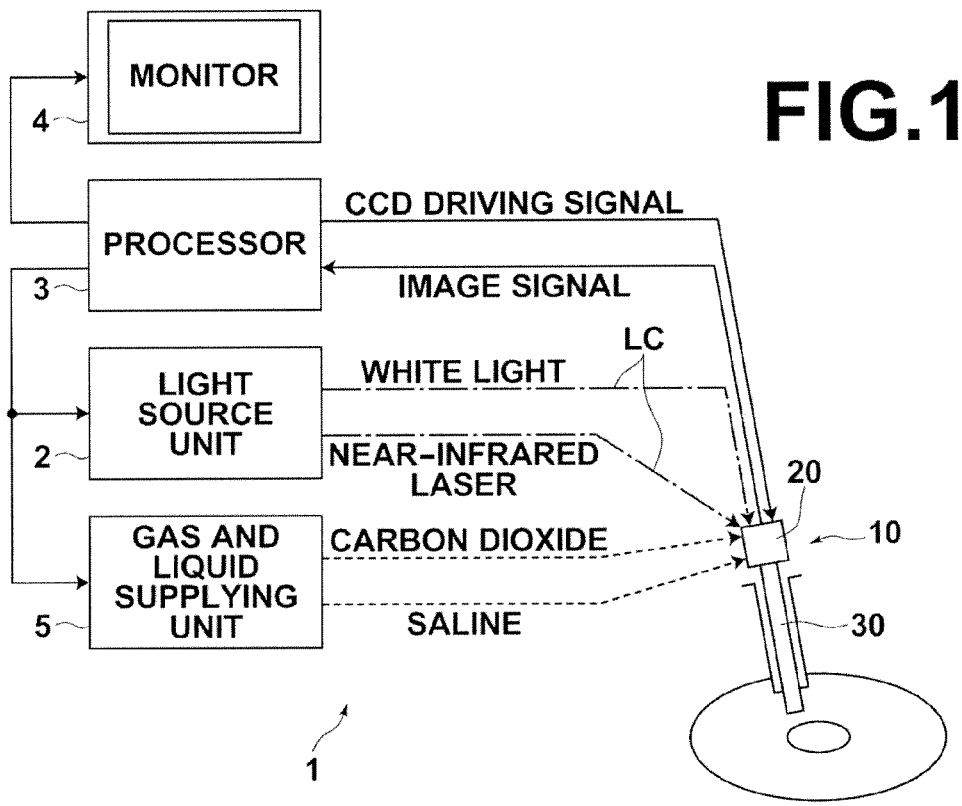
FIG. 1 is a diagram illustrating the schematic configuration of a hard endoscope system employing one embodiment of an imaging device of the invention.

Hereinafter, a hard endoscope system employing one embodiment of an imaging device of the present invention will be described in detail with reference to the drawings. This embodiment is characterized by timing of cleaning of a light exit window, which is disposed at the distal end of an insertion section inserted into a body. However, first, the configuration of the entire system is described. FIG. 1 is a diagram illustrating the schematic configuration of a hard endoscope system 1 of this embodiment.

As shown in FIG. 1, the hard endoscope system 1 of this embodiment includes: a light source unit 2 for emitting blue light and near-infrared light; a hard endoscope imaging device 10 for applying white light, which is obtained by applying wavelength conversion to the blue light emitted from the light source unit 2, and the near-infrared light to a part to be observed, and for capturing a normal image, which is based on reflected light reflected from the part to be observed when the white light is applied, and a fluorescence image based on fluorescence emitted from the part to be observed when the near-infrared light is applied; a processor 3 for applying predetermined processing to an image signal captured by the hard endoscope imaging device 10 and for outputting control signals to the light source unit 2 and a gas and liquid supplying unit 5, which will be described later; a monitor 4 for displaying the fluorescence image and the normal image of the part to be observed based on a display control signal generated at the processor 3; and the gas and liquid supplying unit 5 for supplying saline and carbon dioxide gas to the hard endoscope imaging device 10 in response to a control signal from the processor 3.

As shown in FIG. 1, the hard endoscope imaging device 10 includes a body cavity insertion section 30 to be inserted into a body cavity, such as the abdominal cavity or the chest cavity, and an imaging unit 20 for capturing the normal image and the fluorescence image of the part to be observed guided to the imaging unit 20 by the body cavity insertion section 30.

Figure 2:
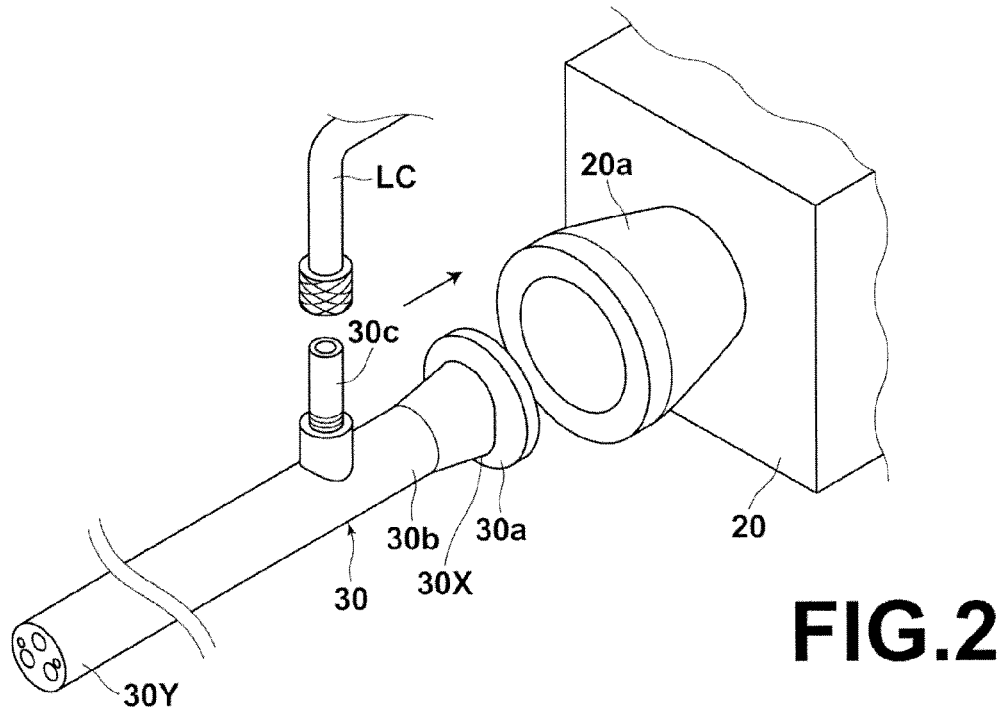
FIG. 2 is a diagram illustrating the schematic structure of a body cavity insertion section.

Further, as shown in FIG. 2, the body cavity insertion section 30 and the imaging unit 20 are removably connected to the hard endoscope imaging device 10. The body cavity insertion section 30 includes a connection member 30a, an insertion member 30b, and a cable connection port 30c.

The connection member 30a is disposed at one end side 30X of the body cavity insertion section 30 (the insertion member 30b), so that the body cavity insertion section 30 is removably connected to the imaging unit 20 when the connection member 30a is fitted in an opening 20a formed at the imaging unit 20, for example.

The insertion member 30b is inserted into the body cavity for imaging the interior of the body cavity. The insertion member 30b is made of a hard material and has a solid cylindrical shape with a diameter of about 5 mm, for example. The insertion member 30b contains a lens group for focusing the image of the part to be observed. The normal image and the fluorescence image of the part to be observed entering via a distal end side 30Y of the insertion member 30b is outputted via the lens group to the imaging unit 20 at the one end side 30X.

The insertion member 30b includes a cable connection port 30c at the lateral side thereof. An optical cable LC is mechanically connected to the cable connection port 30c, thereby optically connecting the light source unit 2 to the insertion member 30b via the optical cable LC.

Figure 3:
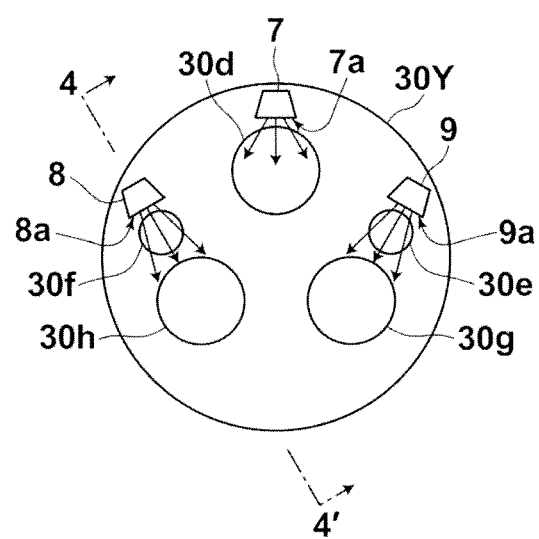
FIG. 3 is a diagram illustrating the schematic structure of a distal end of the body cavity insertion section.

FIG. 3 illustrates the structure of the distal end side 30Y of the body cavity insertion section 30. As shown in FIG. 3, the distal end side 30Y of the body cavity insertion section 30 includes an imaging lens 30d for focusing the normal image and the fluorescence image, and white light applying lenses 30e and 30f for applying the and white light and near-infrared light applying lenses 30g and 30h for applying the near-infrared light, which are disposed substantially symmetrically relative to the imaging lens 30d. The reason for providing the two white light applying lenses 30e and 30f and the two near-infrared light applying lenses 30g and 30h symmetrically relative to imaging lens 30d is to prevent formation of shadow in the normal image and the fluorescence image due to the unlevel shape of the part to be observed.

Further, the distal end side 30Y of the body cavity insertion section 30 includes an imaging lens cleaning nozzle 7, a first light applying lens cleaning nozzle 8 and a second light applying lens cleaning nozzle 9 for discharging the saline and the carbon dioxide gas supplied from the gas and liquid supplying unit 5.

An opening 7a of the imaging lens cleaning nozzle 7 is oriented toward the imaging lens 30d and is adapted to discharge the saline and the carbon dioxide gas toward the imaging lens 30d.

An opening 8a of the first light applying lens cleaning nozzle 8 is oriented toward the white light applying lens 30f and the near-infrared light applying lens 30h and is adapted to discharge the saline and the carbon dioxide gas toward the white light applying lens 30f and the near-infrared light applying lens 30h. An opening 9a of the second light applying lens cleaning nozzle 9 is oriented toward the white light applying lens 30e and the near-infrared light applying lens 30g and is adapted to discharge the saline and the carbon dioxide gas toward the white light applying lens 30e and the near-infrared light applying lens 30g.

Figure 4:
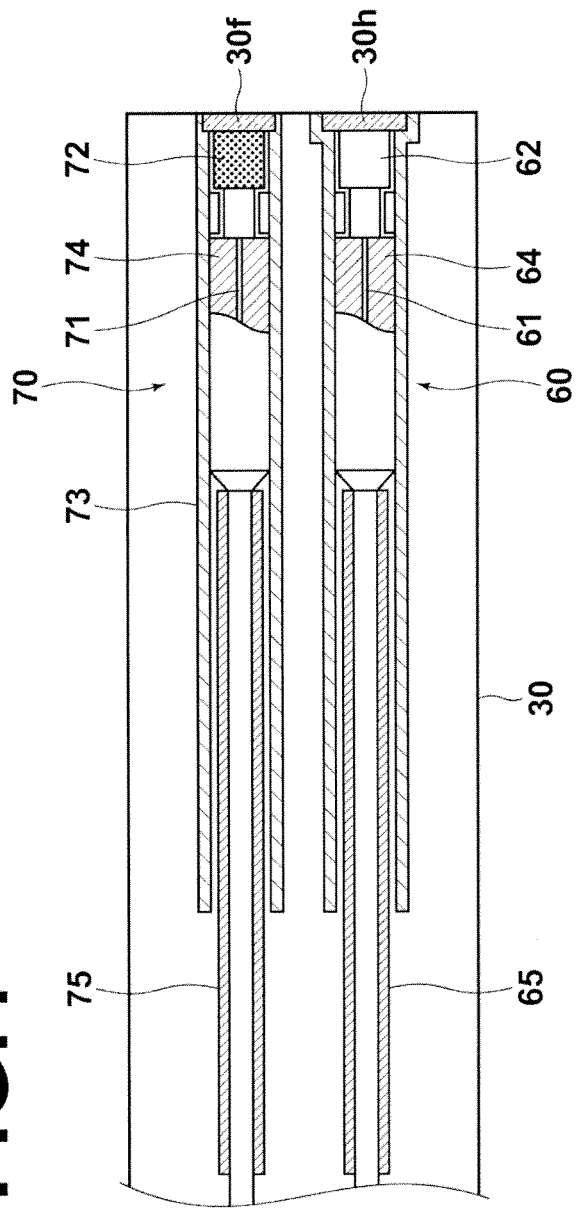
FIG. 4 is a sectional view taken along line 4-4' in FIG. 3.

FIG. 4 is a sectional view taken along line 4-4' in FIG. 3. As shown in FIG. 4, white light applying units 70 (only one is shown in this sectional view) and near-infrared light applying units 60 (only one is shown in this sectional view) are disposed in the body cavity insertion section 30.

The white light applying unit 70 includes a multimode optical fiber 71 for guiding the blue light, and a fluorescent member 72 for emitting visible light ranging from green to yellow when it is excited by absorbing a part of the blue light guided by the multimode optical fiber 71. The fluorescent member 72 is made of a plurality of types of fluorescent materials, such as a YAG fluorescent material or BAM ($BaMgAl_{10}O_{17}$).

A hollow cylindrical sleeve member 73 is disposed to cover the outer periphery of the fluorescent member 72, and a ferrule 74 for holding the multimode optical fiber 71 at the center axis thereof is inserted in the sleeve member 73. Further, a flexible sleeve 75, which covers the coating of the multimode optical fiber 71 extending from the rear end side (the side opposite from the distal end side) of the ferrule 74, is inserted between the multimode optical fiber 71 and the sleeve member 73.

The near-infrared light applying unit 60 includes a multimode optical fiber 61 for guiding the near-infrared light, and a space 62 is provided between the multimode optical fiber 61 and the near-infrared light applying lens 30h.

Similarly to the white light applying unit 70, the near-infrared light applying unit 60 is provided with a hollow cylindrical sleeve member 63, which is disposed to cover the outer periphery of the space 62, and is provided with a ferrule 64 and a flexible sleeve 65.

As the multimode optical fiber used in each light applying unit, a thin optical fiber having a core diameter of 105 μm, a cladding diameter of 125 μm, and a diameter including a protective layer, which serves as the coating, ranging from 0.3 mm to 0.5 mm may be used, for example.

The structures of the white light applying unit including the white light applying lens 30e and the near-infrared light applying unit including the near-infrared light applying lens 30g are the same as those of the white light applying unit 70 including the white light applying lens 30f and the near-infrared light applying unit 60 including the near-infrared light applying lens 30h described above, respectively.

Figure 5:
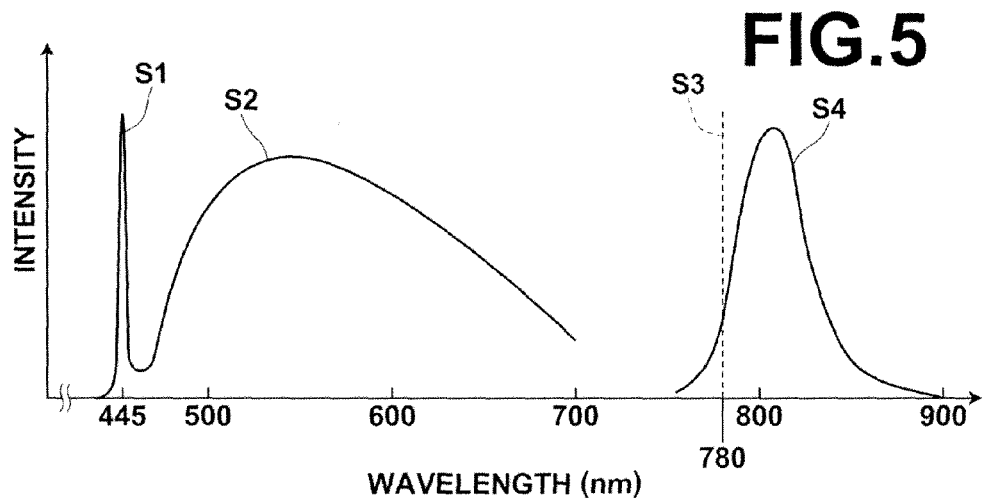
FIG. 5 is a diagram illustrating spectra of light applied by each light applying unit of the body cavity insertion section, of fluorescence emitted from a part to be observed when the light is applied and of reflected light reflected from the part to be observed.

FIG. 5 shows spectra of light applied by each light applying unit to the part to be observed, of fluorescence emitted from the part to be observed when the light is applied, and of reflected light reflected from the part to be observed when the light is applied. Specifically, FIG. 5 shows a blue light spectrum S1 that is transmitted through the fluorescent member 72 of each white light applying unit 70 and applied, a visible light spectrum S2 ranging from green to yellow that is excited at the fluorescent member 72 of the white light applying unit 70 and applied, a near-infrared light spectrum S3 that is applied by the near-infrared light applying unit 60, and an ICG fluorescence spectrum S4 that is emitted when the near-infrared light spectrum S3 is applied by the near-infrared light applying unit 60.

It should be noted that the white light herein is not limited to white light that strictly contains all the wavelength components of the visible light. The white light may contain light in certain wavelength bands, such as R (red) G (green) and B (blue) of standard light, and may widely include light containing wavelength components ranging from green to red, or light containing wavelength components ranging from blue to green, for example. Therefore, although the white light applying unit 70 applies the blue light spectrum S1 and the visible light spectrum S2, as shown in FIG. 5, the light of these spectra are also regarded as the white light.

Figure 6:
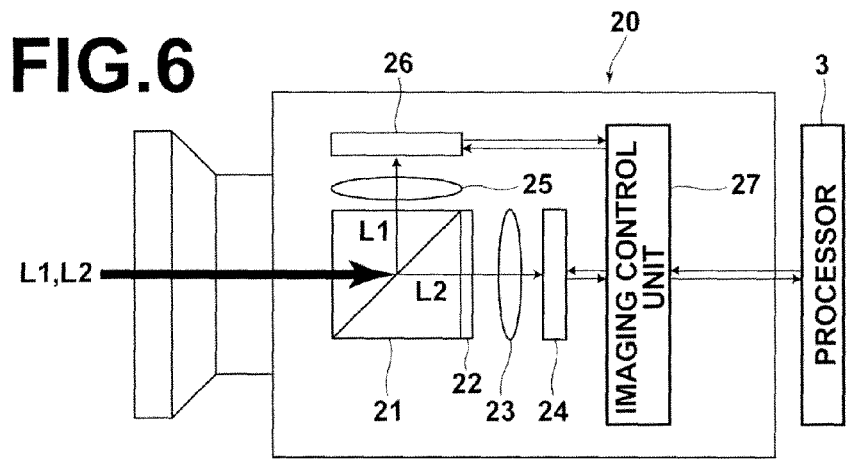
FIG. 6 is a diagram illustrating the schematic configuration of an imaging unit.

FIG. 6 is a diagram illustrating the schematic configuration of the imaging unit 20. The imaging unit 20 includes: a first imaging system for generating a fluorescence image signal of the part to be observed by capturing the fluorescence image of the part to be observed focused by the lens group in the body cavity insertion section 30; and a second imaging system for generating a normal image signal by capturing the normal image of the part to be observed focused by the lens group in the body cavity insertion section 30. A dichroic prism 21, which has spectral characteristics to reflect the normal image and transmit the fluorescence image, divides the optical axis into two perpendicular optical axes directed to these imaging systems, respectively.

The first imaging system includes: a near-infrared cut filter 22 for transmitting the fluorescence image outputted from the body cavity insertion section 30 and cutting the near-infrared light; a first focusing optical system 23 for focusing a fluorescence image L2 that is outputted from the body cavity insertion section 30 and transmitted through the dichroic prism 21 and the near-infrared cut filter 22; and a high-sensitivity image pickup device 24 for capturing the fluorescence image L2 focused by the first focusing optical system 23.

The second imaging system includes: a second focusing optical system 25 for focusing a normal image L1 that is outputted from the body cavity insertion section 30 and reflected from the dichroic prism 21; and an image pickup device 26 for capturing the normal image L1 focused by the second focusing optical system 25.

The high-sensitivity image pickup device 24 detects light in the wavelength band of the fluorescence image L2 with high sensitivity, converts the detected light into the fluorescence image signal and outputs the fluorescence image signal. The high-sensitivity image pickup device 24 is a monochrome image pickup device.

The image pickup device 26 detects light in the wavelength band of the normal image, converts the detected light into the normal image signal and outputs the normal image signal. The image pickup device 26 includes, at the imaging area thereof, color filters of three primary colors, i.e., red (R), green (G) and blue (B), arranged in a Bayer array or in a honeycomb array.

Figure 7:
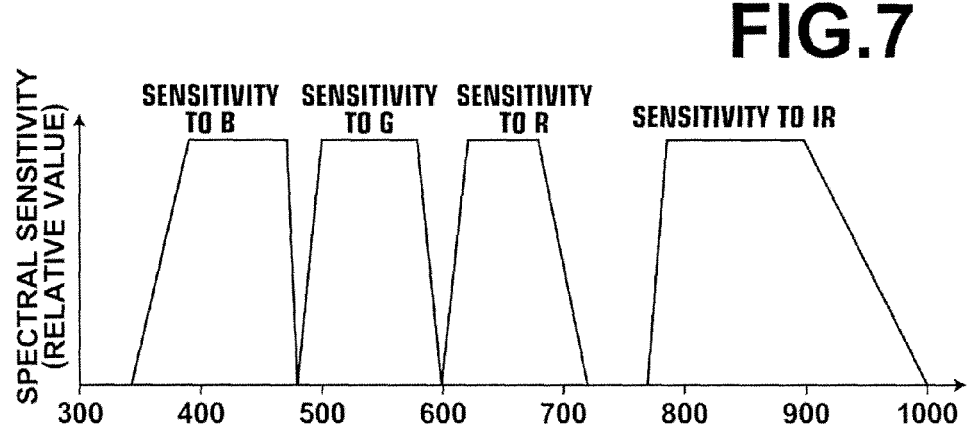
FIG. 7 is a diagram illustrating spectral sensitivity of the imaging unit.

FIG. 7 shows a graph of the spectral sensitivity of the imaging unit 20. Specifically, in the imaging unit 20, the first imaging system is sensitive to IR (near-infrared) and the second imaging system is sensitive to R (red), G (green) and B (blue).

The imaging unit 20 includes an imaging control unit 27. The imaging control unit 27 controls driving of the high-sensitivity image pickup device 24 and the image pickup device 26 based on a CCD driving signal outputted from the processor 3, applies CDS/AGC (correllated double sampling/automatic gain control) and A/D conversion to the fluorescence image signal outputted from the high-sensitivity image pickup device 24 and the normal image signal outputted from the image pickup device 26, and outputs the processed signals to the processor 3 via the cable.

Figure 8:
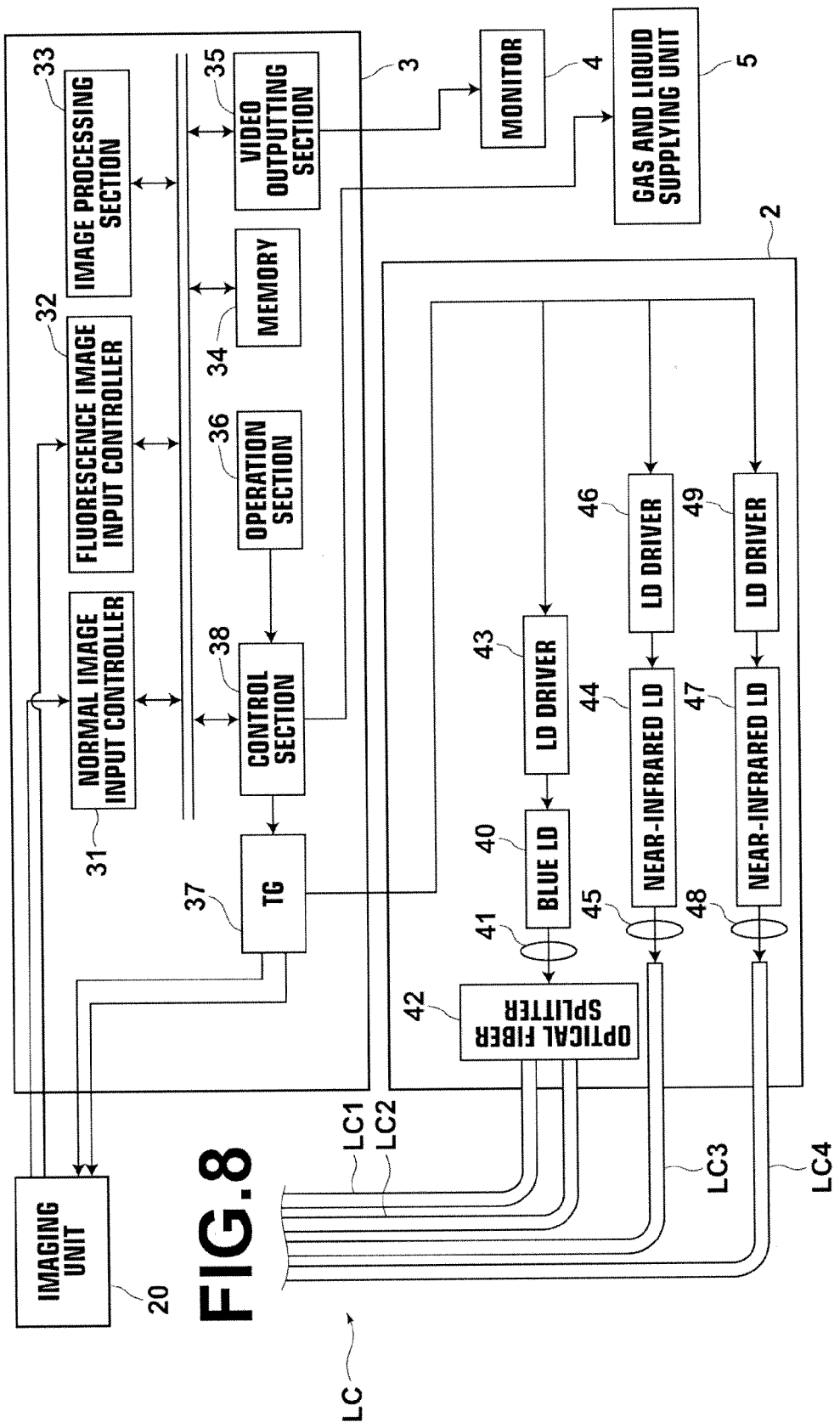
FIG. 8 is a diagram illustrating the schematic configuration of an image processing device and a light source unit.

FIG. 8 is a diagram illustrating the schematic configuration of the light source unit 2 and the processor 3. As shown in FIG. 8, the processor 3 include a normal image input controller 31, a fluorescence image input controller 32, an image processing section 33, a memory 34, a video outputting section 35, an operation section 36, a TG (timing generator) 37 and a control section 38.

The normal image input controller 31 and the fluorescence image input controller 32 includes line buffers with a predetermined capacity for temporarily storing the normal image signal per frame and the fluorescence image signal per frame, respectively, outputted from the imaging control unit 27 of the imaging unit 20. Then, the normal image signal stored at the normal image input controller 31 and the fluorescence image stored at the fluorescence image signal input controller 32 are stored in the memory 34 via a bus.

The image processing section 33 receives the normal image signal per frame and fluorescence image signal per frame read out from the memory 34, applies predetermined image processing to these image signals, and outputs the processed image signals to the bus.

The video outputting section 35 receives the normal image signal and the fluorescence image signal outputted from the image processing section 33 via the bus, applies predetermined processing to each signal to generate a display control signal, and outputs the display control signal to the monitor 4.

The operation section 36 receives inputs by the operator, such as an instruction to start application of the near-infrared light, i.e., an instruction to switch from a normal imaging mode to a fluorescence imaging mode, control parameters, etc. It should be noted that, although the operation section 36 receives the instruction to start application of the near-infrared light in this embodiment, this is not intended to limit the invention. For example, the instruction to start application of the near-infrared light may be received when a foot pedal is pressed.

The TG 37 outputs drive pulse signals for driving the high-sensitivity image pickup device 24 and the image pickup device 26 of the imaging unit 20, and LD drivers 43, 46 and 49 (which will be described later) of the light source unit 2.

The control section 38 controls the entire system. In this embodiment, in particular, the control section 38 outputs a control signal to the gas and liquid supplying unit 5 to supply liquid in response to the signal of the instruction to start application of the near-infrared light received by the operation section 36. The control of liquid supply in conjunction with the application of the near-infrared light is set in advance as a near-infrared light emission-linked mode. In this embodiment, the near-infrared light emission-linked mode can be turned on or off by the operator via the operation section 36.

As shown in FIG. 8, the light source unit 2 includes: a blue LD light source 40 for emitting blue light of 445 nm; a condenser lens 41 for condensing the blue light emitted from the blue LD light source 40 and inputting the condensed blue light to an optical fiber splitter 42; the optical fiber splitter 42 for simultaneously inputting the blue light from the condenser lens 41 to an optical cable LC1 and an optical cable LC2; and a LD driver 43 for driving the blue LD light source 40.

Each of the optical cables LC1 and LC2 is optically connected to the multimode optical fiber 71 of the white light applying unit 70.

The light source unit 2 further includes: near-infrared LD light sources 44 and 47 for emitting near-infrared light ranging from 750 to 790 nm; condenser lenses 45 and 48 for condensing the near-infrared light emitted from the near-infrared LD light sources 44 and 47 and inputting the condensed near-infrared light to optical cables LC3 and LC4, respectively; and LD drivers 46 and 49 for driving the near-infrared LD light sources 44 and 47, respectively.

Each of the optical cables LC3 and LC4 is optically connected to the multimode optical fiber 61 of the near-infrared light applying unit 60.

It should be noted that, although the near-infrared light is used as the excitation light in this embodiment, the excitation light is not limited to the near-infrared light described above. The excitation light is determined as appropriate depending on the type of the fluorescent dye administered into the subject or the type of the living tissue caused to emit fluorescence from itself.

Further, although the laser light sources are used in this embodiment, LED light sources may be used.

Figure 9:
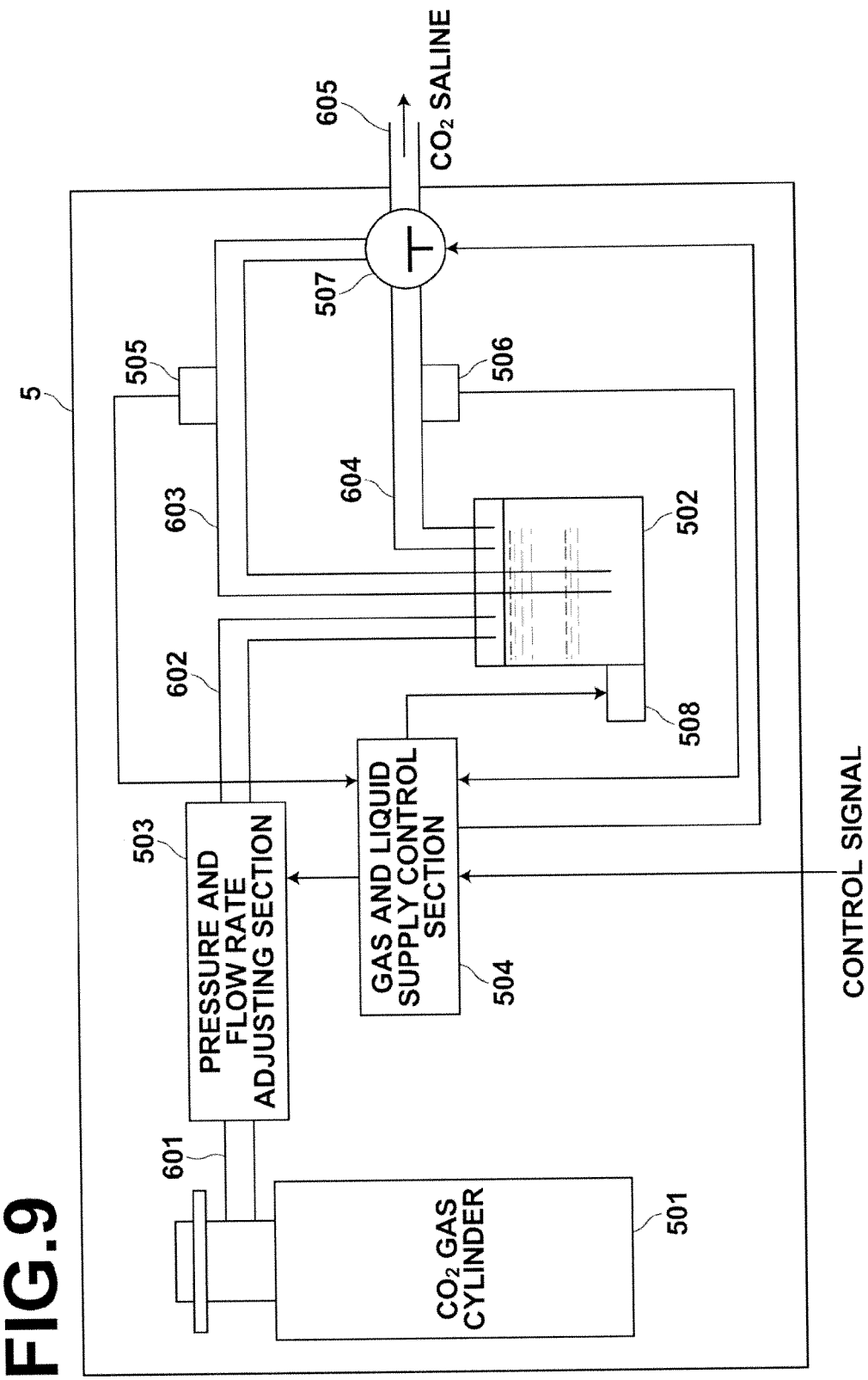
FIG. 9 is a diagram illustrating the schematic configuration of a gas and liquid supplying unit.

FIG. 9 is a block diagram illustrating the schematic configuration of the gas and liquid supplying unit 5. As shown in FIG. 9, the gas and liquid supplying unit 5 includes a $CO_2$ gas cylinder 501, a liquid reservoir 502, a pressure and flow rate adjusting section 503, a gas and liquid supply control section 504, flow sensors 505 and 506, a three-way valve 507 and a heater section 508.

The $CO_2$ gas cylinder 501 stores $CO_2$ gas. The $CO_2$ gas in the $CO_2$ gas cylinder 501 is fed to the pressure and flow rate adjusting section 503 via a conduit 601. The pressure and flow rate adjusting section 503 adjusts the pressure and flow rate of the $CO_2$ gas and supplies the $CO_2$ gas to the liquid reservoir 502 via a conduit 602. The liquid reservoir 502 stores saline, for example, and is adapted to supply the saline to a conduit 603 by means of the $CO_2$ gas supplied via the conduit 602. The liquid reservoir 502 is also adapted to supply the $CO_2$ gas to a conduit 604.

The three-way valve 507 switches between the saline fed from the conduit 603 and the $CO_2$ gas fed from the conduit 604 to supply one of them to the gas and liquid supply conduit 605. The saline or the $CO_2$ gas is supplied to the imaging lens cleaning nozzle 7, the first light applying lens cleaning nozzle 8 and the second light applying lens cleaning nozzle 9 via the gas and liquid supply conduit 605.

The flow sensor 505 detects the flow rate of the saline flowing through the conduit 603. The flow sensor 506 detects the flow rate of the $CO_2$ gas flowing through the conduit 604.

The heater section 508 serves to keep the saline in the liquid reservoir 502 at a predetermined temperature, and includes a temperature sensor therein.

The gas and liquid supply control section 504 controls the pressure and flow rate adjusting section 503, the three-way valve 507 and the heater section 508 based on the control signals outputted from the control section 38 of the processor 3 and detection signals from the flow sensors 505 and 506.

Figure 10:
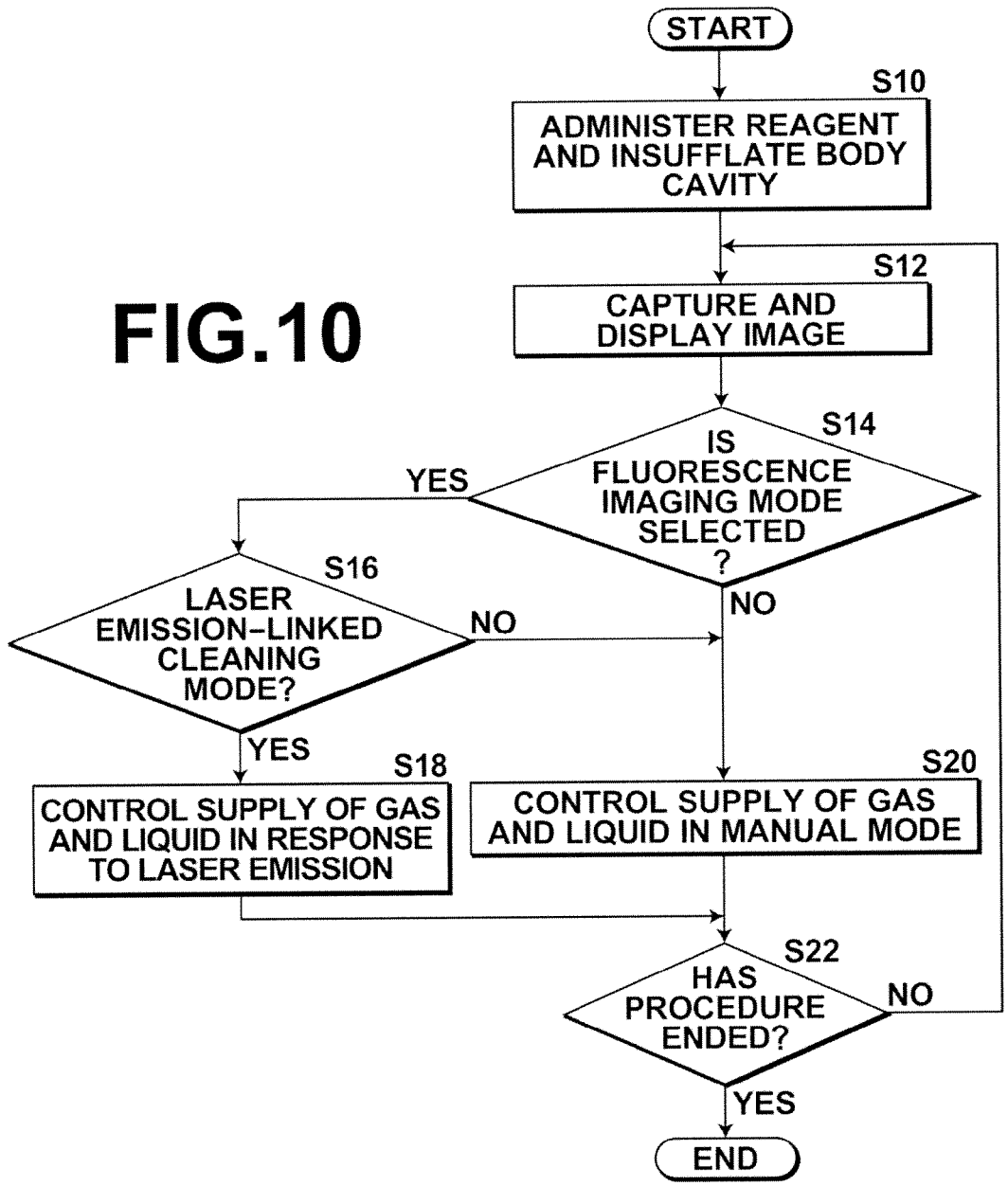
FIG. 10 is a flow chart for explaining operation of the hard endoscope system employing one embodiment of the imaging device of the invention.

Next, operation of the hard endoscope system of this embodiment is described with reference to the flow chart shown in FIG. 10.

First, a labeling reagent is administered into the subject through the vein of the subject, and the $CO_2$ gas is supplied to the subject by the gas and liquid supplying unit 5 to insufflate the body cavity. At this time, the gas and liquid supply control section 504 controls the heater section 508 to keep the saline at a predetermined temperature (S10).

Then, the operator selects the normal imaging mode via the operation section 36 of the processor 3, and a signal indicating the selection is received by the control section 38. Then, the control section 38 controls the components of the system to capture and display the normal image (S12).

In the case where the normal imaging mode is selected, the blue light emitted from the blue LD light source 40 of the light source unit 2 is simultaneously inputted to the optical cables LC1 and LC2 via the condenser lens 41 and the optical fiber splitter 42. Then, the blue light is guided by the optical cables LC1 and LC2 to enter the body cavity insertion section 30, and is guided by the multimode optical fiber 71 of the white light applying unit 70 in the body cavity insertion section 30. Then, a part of the blue light emitted from the emitting end of the multimode optical fiber 71 is transmitted through the fluorescent member 72 to be applied to the part to be observed, and the remaining part of the blue light is subjected to the wavelength conversion by the fluorescent member 72 to be converted into the visible light ranging from green to yellow, and the visible light is applied to the part to be observed. That is, the white light formed by the blue light and the visible light ranging from green to yellow is applied to the part to be observed.

Then, the normal image reflected from the part to be observed when the white light is applied enters the imaging lens 30d at the distal end 30Y of the insertion member 30b and is guided by the lens group in the insertion member 30b to be outputted to the imaging unit 20.

The normal image entered the imaging unit 20 is reflect by the dichroic prism 21 at right angle, and is focused by the second focusing optical system 25 on the imaging area of the image pickup device 26 to be captured by the image pickup device 26.

Then, R, G and B image signals are respectively outputted from the image pickup device 26 and are subjected to CDS/AGC (correllated double sampling/automatic gain control) and A/D conversion at the imaging control unit 27, and the processed signals are outputted to the processor 3 via the cable 5.

Then, the normal image inputted to the signal processor 3 is temporarily stored at the normal image input controller 31, and then is stored in the memory 34. Then, each normal image signal per frame read out from the memory 34 is subjected to tone correction and sharpness correction at the image processing section 33, and is sequentially outputted to the video outputting section 35.

The video outputting section 35 applies predetermined processing to each normal image signal inputted thereto to generate the display control signal, and sequentially outputs the display control signal per frame to the monitor 4. Then, the monitor 4 displays the normal image based on the display control signal inputted thereto.

If the operator, such as a doctor, wishes to capture a fluorescence image of the desired part to be observed in the state where the normal image is displayed as described above, the imaging mode is switched to the fluorescence imaging mode (S14, YES).

The instruction to switch the imaging mode to the fluorescence imaging mode is made via the operation section 36. In response to the instruction to switch the imaging mode, the control signal to start emission of the near-infrared light is outputted from the control section 38 via the TG 37 to the LD drivers 46 and 49 for driving the near-infrared LD light sources 44 and 47. In response to the control signal, the LD drivers 46 and 49 cause the near-infrared light LD light sources 44 and 47 to emit the near-infrared light.

On the other hand, when the instruction to switch the imaging mode to the fluorescence imaging mode is made via the operation section 36, the control section 38 checks whether or not the near-infrared light emission-linked mode is set for the liquid supply from the first light applying lens cleaning nozzle 8 and the second light applying lens cleaning nozzle 9 (S16).

If the near-infrared light emission-linked mode is set (S16, YES), the control section 38 outputs a control signal to the gas and liquid supply control section 504 of the gas and liquid supplying unit 5 in response to the reception of the instruction to switch the imaging mode to the fluorescence imaging mode. Then, in response to the inputted control signal, the gas and liquid supplying unit 5 starts to supply the saline (S18).

Specifically, the pressure and flow rate adjusting section 503 adjusts the pressure and flow rate of the $CO_2$ gas from the $CO_2$ gas cylinder 501, and the $CO_2$ gas is supplied to the liquid reservoir 502 via the conduit 602. This supply of the gas causes the saline in the liquid reservoir 502 to be supplied to the conduit 603.

Then, the saline flows through the conduit 603 and passes through the three-way valve 507 to be supplied to the gas and liquid supply conduit 605, and is supplied via the gas and liquid supply conduit 605 to the imaging lens cleaning nozzle 7, the first light applying lens cleaning nozzle 8 and the second light applying lens cleaning nozzle 9. The imaging lens cleaning nozzle 7, the first light applying lens cleaning nozzle 8 and the second light applying lens cleaning nozzle 9 discharge the saline to clean the white light applying lenses 30e and 30f, the near-infrared light applying lenses 30g and 30h and the imaging lens 30d.

Then, in conjunction with the above-described cleaning of the lenses, the operation to capture the fluorescence image is started. Specifically, the near-infrared light emitted from each of the near-infrared LD light sources 44 and 47 of the light source unit 2 enters the optical cable LC3, LC4 via the condenser lens 45, 48, and enters the body cavity insertion section 30 via the optical cable LC3, LC4. Then, the near-infrared light is guided by the multimode optical fiber 61 of the near-infrared light applying unit 60 in the body cavity insertion section 30 to be applied to the part to be observed.

Then, the ICG fluorescence image emitted from the part to be observed when the near-infrared light serving as the excitation light is applied enters the imaging lens 30d at the distal end 30Y of the insertion member 30b, is guided by the lens group in the insertion member 30b, and is outputted to the imaging unit 20.

The ICG fluorescence image inputted to the imaging unit 20 is transmitted through the dichroic prism 21 and the near-infrared cut filter 22, and is focused by the first focusing optical system 23 on the imaging area of the high-sensitivity image pickup device 24 to be captured by the high-sensitivity image pickup device 24. The ICG fluorescence image signal outputted from high-sensitivity image pickup device 24 is subjected to CDS/AGC (correllated double sampling/automatic gain control) and A/D conversion at the imaging control unit 27, and then is outputted to the processor 3 via the cable 5.

The fluorescence image signal inputted to the processor 3 is temporarily stored at the fluorescence image input controller 32, and then is stored in the memory 34. Then, each fluorescence image signal per frame read out from the memory 34 is subjected to predetermined image processing at the image processing section 33 and is sequentially outputted to the video outputting section 35.

Then, the video outputting section 35 applies predetermined processing to each fluorescence image signal inputted thereto to generate the display control signal, and sequentially outputs the display control signal per frame to the monitor 4. Then, the monitor 4 displays the fluorescence image based on the display control signal inputted thereto.

In contrast, if it is determined in S16 that the near-infrared light emission-linked mode is not set (S16, NO), no liquid supply control is carried out at this time, and supply of the gas and liquid is controlled in a manual mode, which will be described later.

Returning to S14, if it is determined that the fluorescence imaging mode is not selected, i.e., if the normal imaging mode is continuously selected, emission of the saline, or the like, from the imaging lens cleaning nozzle 7, the first light applying lens cleaning nozzle 8 and the second light applying lens cleaning nozzle 9 is controlled by the operator in the manual mode.

Specifically, for example, when the operator determines based on the normal image that there is adhesion of contaminants, and the operator operates the gas and liquid supply switch via the operation section 36 of the processor 3, the gas and liquid supply control section 504 controls the pressure and flow rate adjusting section 503 and the three-way valve 507 to supply the gas and liquid according to the manual operation.

Specifically, when the operator has made an operation to supply the saline from the imaging lens cleaning nozzle 7, the first light applying lens cleaning nozzle 8 and the second light applying lens cleaning nozzle 9, the pressure and flow rate adjusting section 503 adjusts the pressure and flow rate of the $CO_2$ gas in the $CO_2$ gas cylinder 501, and the $CO_2$ gas is supplied to the liquid reservoir 502 via the conduit 602. This supply of the gas causes the saline in the liquid reservoir 502 to be supplied to the conduit 603.

Then, the saline flows through the conduit 603 and passes through the three-way valve 507 to be supplied to the gas and liquid supply conduit 605, and is supplied via the gas and liquid supply conduit 605 to the imaging lens cleaning nozzle 7, the first light applying lens cleaning nozzle 8 and the second light applying lens cleaning nozzle 9 to be discharged therefrom.

Further, when the operator has made an operation to supply gas from the imaging lens cleaning nozzle 7, the first light applying lens cleaning nozzle 8 and the second light applying lens cleaning nozzle 9, the three-way valve 507 is switched to connect to the conduit 604, and the $CO_2$ gas passed through the liquid reservoir 502 is supplied to the conduit 604. Then, the supplied $CO_2$ gas passes through the three-way valve 507 to be supplied to the gas and liquid supply conduit 605, and is supplied via the gas and liquid supply conduit 605 to the imaging lens cleaning nozzle 7, the first light applying lens cleaning nozzle 8 and the second light applying lens cleaning nozzle 9 to be discharged therefrom.

The above-described operations in S12 to 320 are repeated until the procedure with the hard endoscope system 1 ends (322).

It should be noted that, although the imaging mode is switched between the normal imaging mode and the fluorescence imaging mode in the above-described hard endoscope system of the first embodiment, this is not intended to limit the invention. Selection of both the normal imaging mode and the fluorescence imaging mode may be received to carry out operations to capture the normal image and the fluorescence image at the same time. Also in this case, the control section 38 checks whether or not the near-infrared light emission-linked mode is set for capturing the fluorescence image, and if the near-infrared light emission-linked mode is set, the saline is discharged from the imaging lens cleaning nozzle 7, the first light applying lens cleaning nozzle 8 and the second light applying lens cleaning nozzle 9 in conjunction with the emission of the near-infrared light, as described above. In contrast, if the near-infrared light emission-linked mode is not set, the gas and liquid supply is controlled in the manual mode.

Further, although both the imaging lens 30d and the near-infrared light applying lenses 30g and 30h are cleaned in conjunction with the emission of the near-infrared light when the near-infrared light emission-linked mode is set in the above-described embodiment, this is not intended to limit the invention. In that case, only the near-infrared light applying lenses 30g and 30h may be cleaned, and the cleaning of the imaging lens 30d may not be carried out in conjunction with the emission of the near-infrared light.

Figure 11:
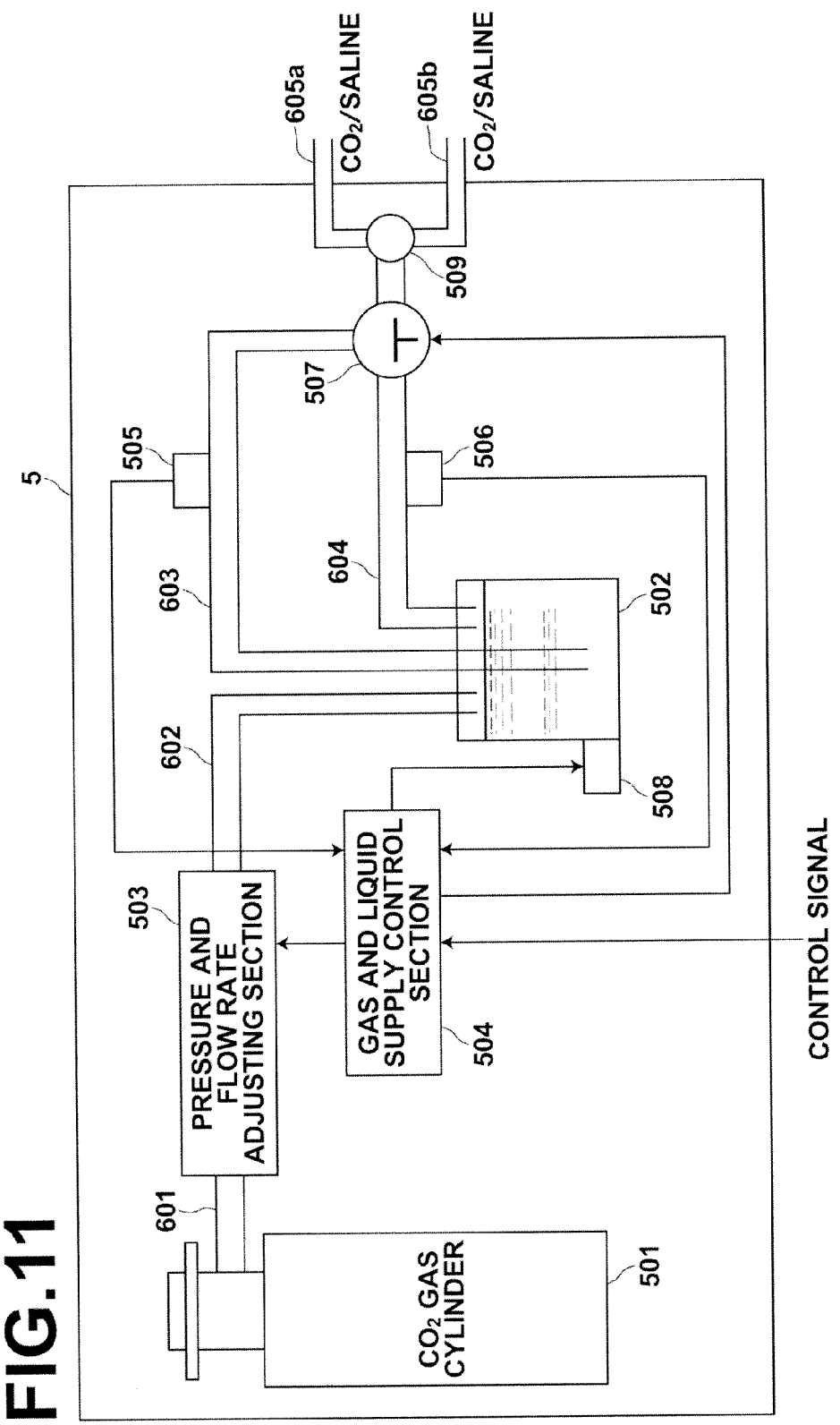
FIG. 11 is a diagram illustrating the schematic configuration of another embodiment of the gas and liquid supplying unit.

Specifically, as shown in FIG. 11, for example, a two-way valve 509 may be provided downstream the three-way valve 507, so that when the instruction to switch the imaging mode to the fluorescence imaging mode is made, the saline may be discharged only from the first and second light applying lens cleaning nozzles 8 and 9 via a conduit 605a for cleaning of the light applying lenses without supplying the saline to a conduit 605b for cleaning of the imaging lens.

By not carrying out cleaning the imaging lens 30d in this manner, such a situation that the operation to capture the normal image or the fluorescence image is inadvertently hindered by the cleaning liquid (saline) is prevented, thereby preventing the operator from being bothered by such hindrance.

In this case, the cleaning of the imaging lens 30d may be carried out, for example, in the manual mode, as described above.

Further, an instruction indicating whether or not the cleaning of the imaging lens 30d is carried out in conjunction with the emission of the near-infrared light may be received, and the cleaning of the imaging lens 30d may be linked to the emission of the near-infrared light or the manual mode may be selected based on the instruction.

Figure 12:
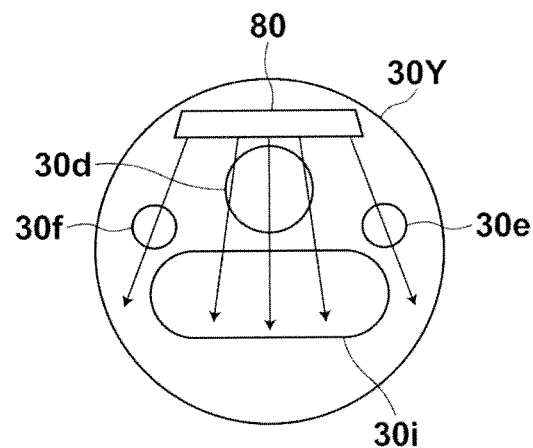
FIG. 12 is a diagram illustrating a cleaning nozzle of a hard endoscope system employing another embodiment of the imaging device of the invention.

Still further, although the three cleaning nozzles including the imaging lens cleaning nozzle 7, the first light applying lens cleaning nozzle 8 and the second light applying lens cleaning nozzle 9 are provided in the above-described embodiment, this is not intended to limit the invention. For example, as shown in FIG. 12, a single cleaning nozzle 80 may be used for cleaning of all the lenses. In the embodiment shown in FIG. 12, only one near-infrared light applying unit 60 is provided, and an ellipsoidal near-infrared light applying lens 30i is provided to widen the light application range.

Figure 13:
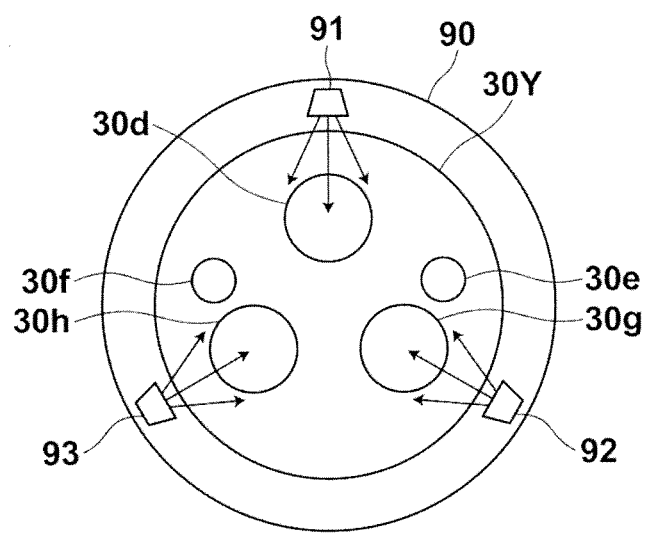
FIG. 13 is a diagram illustrating cleaning nozzles of a hard endoscope system employing still another embodiment of the imaging device of the invention.

Yet further, although the gas and liquid supply conduit is inserted in the body cavity insertion section 30 and the cleaning nozzles are provided at the distal end of the body cavity insertion section 30 in the above-described embodiment, this is not intended to limit the invention. As shown in FIG. 13, the gas and liquid supply conduit may be provided at a mantle tube 90 disposed around the lateral side of the body cavity insertion section 30, and a first cleaning of nozzle 91, a second cleaning of nozzle 92 and a third cleaning of nozzle 93 may be provided at the distal end of the mantle tube 90. Since the mantle tube 90 is not secured to the body cavity insertion section 30, the first to third cleaning nozzle 91, 92 and 93 may be positioned in arbitrary positions along the circumference of the distal end of the body cavity insertion section 30, thereby providing freedom of positions to be cleaned.

Although the imaging device of the invention is applied to the hard endoscope system in the above-described embodiment, this is not intended to limit the invention. For example, the imaging device of the invention may be applied to an endoscopic system including a flexible endoscope device. Besides endoscopic systems, the imaging device of the invention may be applied to a so-called video camera-type medical imaging device, which does not have an insertion section to be inserted into a body.

What is claimed is:

1. A method of cleaning a light exit window of an imaging device, the imaging device including a light applying unit for applying illuminating light emitted from a light source to a part to be observed through the light exit window, and an imaging unit for capturing an image by receiving light coming from the part to be observed when the illuminating light is applied, the method comprising:
 receiving an instruction to start application of the illuminating light; and
 discharging a liquid toward the light exit window in response to the instruction to start application of the illuminating light.

2. An imaging device including a light applying unit for applying illuminating light emitted from a light source to a part to be observed through at least one light exit window, and an imaging unit for capturing an image by receiving light coming from the part to be observed when the illuminating light is applied, the imaging device further comprising:
 a light exit window cleaning unit for discharging a liquid toward the at least one light exit window; and
 a light-application start instruction receiving unit for receiving an instruction to start application of the illuminating light,
 wherein the light exit window cleaning unit discharges the liquid in response to the instruction to start application of the illuminating light.

3. The imaging device as claimed in claim 2, wherein the light applying unit comprises a body cavity insertion section to be inserted into a body cavity, and the at least one light exit window is provided at a distal end of the body cavity insertion section.

4. The imaging device as claimed in claim 2, wherein the light applying unit applies excitation light serving as the illuminating light to the part to be observed through the at least one light exit window, and the imaging unit captures a fluorescence image by receiving fluorescence emitted from the part to be observed when the excitation light is applied.

5. The imaging device as claimed in claim 2, wherein the light source comprises a laser light source.

6. The imaging device as claimed in claim 2, wherein the light source comprises a light-emitting diode light source.

7. The imaging device as claimed in claim 2, wherein the imaging unit receives the light coming from the part to be observed through an imaging lens, and an imaging lens cleaning unit for discharging the liquid toward the imaging lens is provided separately from the light exit window cleaning unit.

8. The imaging device as claimed in claim 7, wherein, in response to the instruction to start application of the illuminating light, the light exit window cleaning unit discharges the liquid only from the light exit window cleaning unit among the imaging lens cleaning unit and the light exit window cleaning unit.

9. The imaging device as claimed in claim 2, wherein the at least one light exit window comprises an excitation light exit window and a white light exit window, the light applying unit applies excitation light serving as the illuminating light to the part to be observed through the excitation light exit window, and applies white light serving as the illuminating light to the part to be observed through the white light exit window, the imaging unit captures a fluorescence image by receiving fluorescence emitted from the part to be observed when the excitation light is applied, and captures a normal image by receiving reflected light reflected from the part to be observed when the white light is applied, and the light exit window cleaning unit comprises a nozzle for discharging the liquid, and the single nozzle is used to discharge the liquid toward both the excitation light exit window and the white light exit window.

10. The imaging device as claimed in claim 2, wherein the light applying unit applies excitation light serving as the illuminating light to the part to be observed through the excitation light exit window, and applies white light serving as the illuminating light to the part to be observed through the white light exit window, the imaging unit captures a fluorescence image by receiving, through an imaging lens, fluorescence emitted from the part to be observed when the excitation light is applied, and captures a normal image by receiving, through the imaging lens, reflected light reflected from the part to be observed when the white light is applied, and the light exit window cleaning unit comprises a nozzle for discharging the liquid, and the single nozzle is used to discharge the liquid toward the excitation light exit window, the white light exit window and the imaging lens.

11. The imaging device as claimed in claim 2, wherein the light exit window cleaning unit is disposed at a mantle tube provided around the body cavity insertion section.

* * * * *